US00PP10410P

United States Patent [19]

Lemon

[11] Patent Number: Plant 10,410

[45] Date of Patent: May 19, 1998

[54] VARIETY OF GERANIUM PLANT NAMED 'LOLLIPOP'

[75] Inventor: David Lemon, Lompoc, Calif.

[73] Assignee: John Bodger & Sons Company, So. El Monte, Calif.

[21] Appl. No.: 821,259

[22] Filed: Mar. 20, 1997

Related U.S. Application Data

[63] Continuation of Ser. No. 571,170, Dec. 12, 1995, abandoned.

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 6,652 3/1989 Winner ..... Plt./87.12

P.P. 9,305 9/1995 Stoots ..... Plt./87.12

*Primary Examiner*—Howard J. Locker

*Attorney, Agent, or Firm*—Fulwider Patton Lee Utecht, LLP

[57] ABSTRACT

The cultivar is characterized by its dark green foliage and coral bloom. Its strong growth habit, quick rooting time and continuous flowering provide for superb cuttings and also for quick recovery following wet weather conditions. The blooms are slow to shatter and exhibit good post-harvest quality.

1 Drawing Sheet

This application is a continuation of application Ser. No. 08/571,170 filed on Dec. 12, 1995 (now abandoned).

BACKGROUND OF THE NEW PLANT

The present invention comprises a new and distinct cultivar of *Pelargonium×hortorum* known by the varietal name Lollipop (Oglevee No. 1400, Bodger No. 1GM 176-1). The new variety was discovered in a selective breeding program by David Lemon at Bodger Seeds, Ltd., Lompoc, Calif. The new variety is a selection from the crossing of Rio (unpatented) which has a rose-pink/red bicolor flower having a single flower form, is crossed with Capri (U.S. Plant Pat. No. 6,652) which has a light salmon pink flower and includes dark green leaves as distinguished from the claimed cultivar.

The new cultivar was first asexually reproduced by cuttings at Oglevee Ltd., Connellsville, Pa., and has been repeatedly asexually reproduced by cuttings at Oglevee Ltd. in Connellsville, Pa. It has been found to retain its distinctive characteristics through successive propagations.

The new cultivar, when grown in a glass greenhouse in Connellsville, Pa, using full light, 60° F. night temperature, 68° F. day temperature, 72° F. vent temperature and grown in a soilless media of constant fertilizer 200–250 parts per million of nitrogen and potassium has a response time of six weeks from the rooted cutting to a flowering plant in a 10.0 cm pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories were taken on rooted cuttings believed to have been potted on approximately Feb. 18, 1995 and flowering on approximately Apr. 1, 1995 under full light and greenhouse, and colorings were taken indoors under 200–220 foot candles of fluorescent cool white light using the R.H.S. Colour Chart of The Royal Horticultural Society of London.

The Plant

Classification:

*Botanical.*—*Pelargonium×hortorum.*

Form: Semi-dwarf mound.

*Height.*—17.0–19.0 cm above the media surface.

*Growth.*—Basal branching; free flowering.

*Strength.*—Free standing.

Foliage: Stalked leaf attachment; very dark green foliage; no distinct zone present.

Leaves:

*Size.*—8.0–10.5 cm across; fully expanded leaf.

*Shape.*—Reniform; cordate base.

*Margin.*—Crenate.

*Texture.*—Pubescent; slightly reflective; leathery.

*Color.*—Top: Yellow/Green Group 147A; Zone: Not present (although a true dark leaf, the zone is not generally perceived as distinct but depends upon the cultural conditions. Bottom: Green Group 137B.

*Ribs and veins.*—Palmate venation; Color: Yellow/Green group 146C.

Petioles:

*Length.*—7.5–9.0 cm.

*Color.*—Green group 137C.

Stem:

*Color.*—Yellow/green group 146B.

*Internodes.*—1.5–3.0 cm in length.

The Bud

Shape: Upright; hemispherical cluster.

Size: 2.0–3.5 cm across.

Inflorescence

Blooming habit: Continuous blooming; semi-double.

Size: 9.5–11.0 cm across.

Borne: Umbel; florets on pedicel; pedicel on peduncle; 6.5–9.0 cm above foliage.

Florets:

*Closed.*—Bud size: 0.5–0.7 cm across, 0.09–1.0 cm in length; elliptical; bud just showing color.

*Open.*—Form — Flat to slightly cupped; petaloids present; 13 florets per inflorescence. Color — Upper petal surface: Lower petal surface: Red Group 40A; Red Group 43C. Petals — 6–8 in number; some twisted. Size — 3.5–4.5 cm. Texture and appearance — Velvety and smooth; appearance from a distance is that of a rich dark coral bloom above very dark green foliage.

Petaloids:

*Quantity.*—1–3.

*Shape.*—Some flat; some twisted and elongated; some with pollen attached (the structure may not change completely to a full petaloid form and may retain some anther characteristics);

*Color.*—Top: Red Group 40A; Bottom: Red Group 43C.

Pedicel:

*Length.*—3.0–3.6 cm.

*Color.*—Greyed/Purple Group 184A.

Peduncle: Arises from the node opposite the leaf petiole.

*Length.*—10.0–15.5 cm.

*Color.*—At the stem base: Yellow/Green Group 146B; shading of Greyed/Purple Group 183A extending from midway up peduncle to umbel attachment.

Persistence:

*Disease resistance.*—Not known.

*Lasting quality.*—slow to shatter; excellent performance in both the greenhouse and outdoors.

Reproductive Organs

Stamens:

*Anthers.*—Length: 2.0–3.0 mm.

*Filaments.*—Length: 7.0–9.0 mm; Color: white with pink tips.

*Pollen.*—Golden Brown.

Pistils:

*Number.*—1.

*Length.*—8.0–9.0 mm.

*Stigma.*—5–6 parted; Color: Red/Purple Group 60C.

*Style.*—Length: 3.0–4.0 mm; Color; Red/Purple Group 60C.

Ovaries: Pubescent.

*Length.*—4.0–5.0 mm.

*Color.*—Yellow/Green Group 146D.

Fruit: None.

General Characteristics

The very dark green foliage of Lollipop makes it is a unique addition to the geranium market. The rich coral bloom and dark green foliage create an attractive combination. Cutting production and rooting time are very similar to the current variety Red Hots (U.S. Plant Pat. No. 9,305) which has a scarlet red flower. The relatively compact nature of Lollipops allows for productive finishing. Outdoor performance is exceptional. Given all those positive properties, this variety should please both the grower and the gardener.

I claim:

1. A new and distinct variety of Geranium plant, substantially as shown and described.

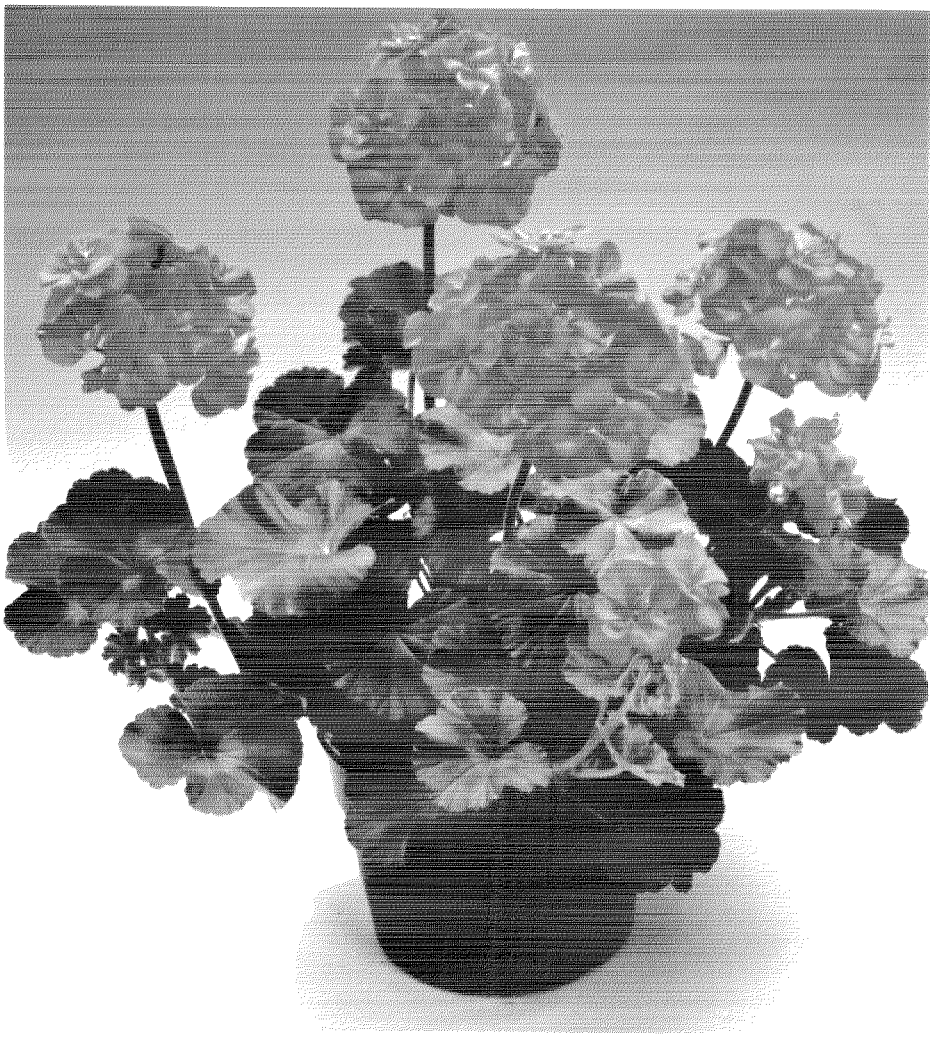

* * * * *